United States Patent
Ceulemens et al.

(10) Patent No.: US 12,097,206 B2
(45) Date of Patent: *Sep. 24, 2024

(54) METHOD FOR THE TREATMENT OF DRAVET SYNDROME

(71) Applicants: KATHOLIEKE UNIVERSITEIT LEUVEN, Leuven (BE); UNIVERSITY HOSPITAL ANTWERP, Edegem (BE)

(72) Inventors: Berten Ceulemens, Leuven (BE); Lieven Lagae, Edegem (BE)

(73) Assignees: Katholieke Universiteit Leuven, Leuven (BE); University Hospital Antwerp, Edegem (BE)

( * ) Notice: Subject to any disclaimer, the term of this patent is extended or adjusted under 35 U.S.C. 154(b) by 74 days.

This patent is subject to a terminal disclaimer.

(21) Appl. No.: 17/667,136

(22) Filed: Feb. 8, 2022

(65) Prior Publication Data
US 2022/0160727 A1   May 26, 2022

Related U.S. Application Data

(63) Continuation of application No. 16/900,055, filed on Jun. 12, 2020, now abandoned, which is a continuation of application No. 15/429,506, filed on Feb. 10, 2017, now abandoned, which is a continuation of application No. 15/003,161, filed on Jan. 21, 2016, now Pat. No. 9,603,815, which is a continuation of application No. 13/887,014, filed on May 3, 2013, now Pat. No. 9,549,909.

(51) Int. Cl.
| | | |
|---|---|---|
| *A61K 31/5513* | (2006.01) | |
| *A61K 31/135* | (2006.01) | |
| *A61K 31/137* | (2006.01) | |
| *A61K 31/19* | (2006.01) | |
| *A61K 31/36* | (2006.01) | |
| *A61K 31/551* | (2006.01) | |
| *A61K 45/06* | (2006.01) | |
| *C12Q 1/6883* | (2018.01) | |

(52) U.S. Cl.
CPC ........ *A61K 31/5513* (2013.01); *A61K 31/135* (2013.01); *A61K 31/137* (2013.01); *A61K 31/19* (2013.01); *A61K 31/36* (2013.01); *A61K 31/551* (2013.01); *A61K 45/06* (2013.01); *C12Q 1/6883* (2013.01); *C12Q 2600/156* (2013.01)

(58) Field of Classification Search
CPC .............. A61K 31/5513; A61K 31/135; A61K 31/137; A61K 31/36; A61K 31/551; C12Q 2600/156
See application file for complete search history.

(56) References Cited

U.S. PATENT DOCUMENTS

| | | |
|---|---|---|
| 3,117,160 A | 1/1964 | Holland |
| 3,198,833 A | 8/1965 | Beregi |
| 3,198,834 A | 8/1965 | Beregi et al. |
| 3,759,979 A | 9/1973 | Beregi et al. |
| 4,309,445 A | 1/1982 | Wurtman |
| 4,452,815 A | 6/1984 | Wurtman |
| 4,824,987 A | 4/1989 | Kleeman |
| 4,857,553 A | 8/1989 | Ward et al. |
| 5,587,398 A | 12/1996 | Elmaleh et al. |
| 5,808,156 A | 9/1998 | Cannata et al. |
| 5,811,586 A | 9/1998 | Cannata et al. |
| 5,834,477 A | 11/1998 | Mioduszewski |
| 5,985,880 A | 11/1999 | Chang |
| 6,045,501 A | 4/2000 | Elsayed et al. |
| 6,315,720 B1 | 11/2001 | Williams et al. |
| 6,561,976 B2 | 5/2003 | Elsayed et al. |
| 6,561,977 B2 | 5/2003 | Williams et al. |
| 6,599,901 B1 | 7/2003 | Flohr |
| 6,755,784 B2 | 6/2004 | Williams et al. |
| 6,869,399 B2 | 3/2005 | Williams et al. |
| 6,908,432 B2 | 6/2005 | Elsayed et al. |
| 7,141,018 B2 | 11/2006 | Williams et al. |
| 7,585,493 B2 | 9/2009 | Hale |
| 7,668,730 B2 | 2/2010 | Reardan et al. |
| 7,714,020 B2 | 5/2010 | Gluckman et al. |
| 7,765,106 B2 | 7/2010 | Reardan et al. |
| 7,765,107 B2 | 7/2010 | Reardan et al. |
| 7,797,171 B2 | 9/2010 | Reardan et al. |
| 7,874,984 B2 | 1/2011 | Elsayed et al. |
| 7,895,059 B2 | 2/2011 | Reardan et al. |
| 7,959,566 B2 | 6/2011 | Williams et al. |

(Continued)

FOREIGN PATENT DOCUMENTS

| | | |
|---|---|---|
| CN | 1425167 | 6/2003 |
| CN | 1634857 A | 7/2005 |

(Continued)

OTHER PUBLICATIONS

Aicardi et al., "Treatment of Self-Induced Photosensitive Epilepsy with Fenfluramine" New England Journal of Medicine (1985) 313:1419.

Aicardi et al., "Syncopal Attacks Compulsively Self-induced by Valsalva's Maneuver Associated with Typical Absence Seizures" Archives of Neurology (1988) 45:923-925.

Anandam, R., Affiliations Indian Journal of Pediatrics (Jan. 1, 2000) 67 (1 Suppl):S88-91 (Abstract Only).

(Continued)

*Primary Examiner* — Shobha Kantamneni
(74) *Attorney, Agent, or Firm* — Bret E. Field; Bozicevic, Field & Francis LLP

(57) ABSTRACT

A method of treating and/or preventing Dravet Syndrome in a patient such as a patient previously diagnosed with Dravet Syndrome, by administering an effective dose of fenfluramine or its pharmaceutically acceptable salt to that patient. Dravet Syndrome patients are typically children under the age of 18 and are treated at a preferred dose of less than about 0.5 to about 0.01 mg/kg/day.

5 Claims, No Drawings

(56) References Cited

U.S. PATENT DOCUMENTS

| | | |
|---|---|---|
| 8,204,763 B2 | 6/2012 | Elsayed et al. |
| 8,263,650 B2 | 9/2012 | Cook et al. |
| 8,315,886 B2 | 11/2012 | Williams et al. |
| 8,386,274 B1 | 2/2013 | Pinsonneault |
| 8,457,988 B1 | 6/2013 | Reardan et al. |
| 8,589,182 B1 | 11/2013 | Reardan et al. |
| 8,589,188 B2 | 11/2013 | Elsayed et al. |
| 8,626,531 B2 | 1/2014 | Williams et al. |
| 8,731,963 B1 | 5/2014 | Reardan et al. |
| 9,125,900 B2 | 9/2015 | Meyer |
| 9,549,909 B2 | 1/2017 | Ceulemens |
| 9,603,814 B2 | 3/2017 | Ceulemens |
| 9,603,815 B2 | 3/2017 | Ceulemens |
| 9,610,260 B2 | 4/2017 | Ceulemens |
| 10,351,509 B2 | 7/2019 | Londesbrough |
| 10,351,510 B2 | 7/2019 | Londesbrough |
| 10,452,815 B2 | 10/2019 | Stewart et al. |
| 10,478,441 B2 | 11/2019 | Ceulemens |
| 10,478,442 B2 | 11/2019 | Ceulemens |
| 10,517,841 B1 | 12/2019 | Galer et al. |
| 10,603,290 B2 | 3/2020 | Farr |
| 10,682,317 B2 | 6/2020 | Abu-Izza |
| 10,689,324 B2 | 6/2020 | Farr |
| 10,947,183 B2 | 3/2021 | Londesbrough et al. |
| 10,950,331 B2 | 3/2021 | Stewart et al. |
| 10,952,976 B2 | 3/2021 | Galer |
| 11,040,018 B2 | 6/2021 | Farr |
| 11,325,882 B2 | 5/2022 | Farr |
| 11,406,606 B2 | 8/2022 | Farr |
| 11,458,111 B2 | 10/2022 | Abu-Izza |
| 11,571,397 B2 | 2/2023 | Martin |
| 11,612,574 B2 | 3/2023 | Galer |
| 11,634,377 B2 | 4/2023 | Londesbrough et al. |
| 11,673,852 B2 | 6/2023 | Farr |
| 11,759,440 B2 | 9/2023 | Farr |
| 11,786,487 B2 | 10/2023 | Farr |
| 2002/0038310 A1 | 3/2002 | Reitberg |
| 2002/0098175 A1 | 7/2002 | Zohoungbogbo |
| 2003/0007934 A1 | 1/2003 | Rabinowitz et al. |
| 2003/0118654 A1 | 5/2003 | Santos et al. |
| 2004/0117205 A1 | 6/2004 | Reardan et al. |
| 2004/0249212 A1 | 12/2004 | Smallridge et al. |
| 2005/0182103 A1 | 8/2005 | Finke et al. |
| 2005/0260610 A1 | 11/2005 | Kurtz et al. |
| 2006/0121066 A1 | 6/2006 | Jaeger et al. |
| 2006/0270611 A1 | 11/2006 | Dries et al. |
| 2007/0123556 A1 | 5/2007 | Pennypacker |
| 2008/0004904 A1 | 1/2008 | Tran |
| 2008/0103179 A1 | 5/2008 | Tam |
| 2008/0243584 A1 | 10/2008 | Srinivasan |
| 2008/0261962 A1 | 10/2008 | Greer |
| 2009/0171697 A1 | 7/2009 | Glauser |
| 2010/0088778 A1 | 4/2010 | Mulley |
| 2010/0298181 A1 | 11/2010 | Hanada et al. |
| 2011/0092535 A1 | 4/2011 | Barnes et al. |
| 2011/0184747 A1 | 7/2011 | Bozic |
| 2011/0212171 A1 | 9/2011 | Venkatesh et al. |
| 2011/0230473 A1 | 9/2011 | Gordon et al. |
| 2012/0065999 A1 | 3/2012 | Takatoku |
| 2012/0107396 A1 | 5/2012 | Khan |
| 2012/0115958 A1 | 5/2012 | Mariotti et al. |
| 2012/0157392 A1 | 6/2012 | Martin et al. |
| 2012/0270848 A1 | 10/2012 | Mannion |
| 2012/0303388 A1 | 11/2012 | Vishnubhatla |
| 2013/0079336 A1 | 3/2013 | Mott et al. |
| 2013/0218586 A1 | 8/2013 | Huser |
| 2013/0296398 A1 | 11/2013 | Whalley |
| 2014/0030343 A1 | 1/2014 | Lamson |
| 2014/0142140 A1 | 5/2014 | Bird |
| 2014/0162942 A1 | 6/2014 | Ghosal |
| 2014/0329908 A1 | 11/2014 | Ceulemens et al. |
| 2014/0343044 A1 | 11/2014 | Ceulemens et al. |
| 2014/0343162 A1 | 11/2014 | Ceulemens et al. |
| 2014/0348966 A1 | 11/2014 | Balemba |
| 2015/0080377 A1 | 3/2015 | Dhanoa |
| 2015/0291597 A1 | 10/2015 | Mannion |
| 2015/0310187 A1 | 10/2015 | Rabinowitz |
| 2015/0359755 A1 | 12/2015 | Guy et al. |
| 2016/0136114 A1 | 5/2016 | Ceulemens et al. |
| 2016/0228454 A1 | 8/2016 | Zhang et al. |
| 2016/0249863 A1 | 9/2016 | Ando |
| 2016/0279159 A1 | 9/2016 | Hirano et al. |
| 2017/0020885 A1 | 1/2017 | Hsu |
| 2017/0056344 A1 | 3/2017 | Farr et al. |
| 2017/0071940 A1 | 3/2017 | Olaleye et al. |
| 2017/0071949 A1 | 3/2017 | De Witte et al. |
| 2017/0135594 A1 | 5/2017 | Hartings et al. |
| 2017/0151194 A1 | 6/2017 | Ceulemens |
| 2017/0151214 A1 | 6/2017 | Ceulemens et al. |
| 2017/0151257 A1 | 6/2017 | Ceulemens |
| 2017/0151259 A1 | 6/2017 | Ceulemens |
| 2017/0174613 A1 | 6/2017 | Londesbrough et al. |
| 2017/0174614 A1 | 6/2017 | Farr et al. |
| 2017/0348303 A1 | 12/2017 | Bosse |
| 2018/0028499 A1 | 2/2018 | Baraban et al. |
| 2018/0055789 A1 | 3/2018 | Farr |
| 2018/0092864 A1 | 4/2018 | Martin et al. |
| 2018/0141953 A1 | 5/2018 | Dax |
| 2018/0148403 A1 | 5/2018 | Londesbrough et al. |
| 2018/0215701 A1 | 8/2018 | Carroll et al. |
| 2018/0221319 A1 | 8/2018 | During |
| 2018/0271821 A1 | 9/2018 | Gold |
| 2018/0325909 A1 | 11/2018 | DeWitte |
| 2019/0083425 A1 | 3/2019 | Farr |
| 2019/0091173 A1 | 3/2019 | Farfel |
| 2019/0091174 A1 | 3/2019 | Galer |
| 2019/0091175 A1 | 3/2019 | Morrison |
| 2019/0091176 A1 | 3/2019 | Galer |
| 2019/0091177 A1 | 3/2019 | Galer |
| 2019/0091179 A1 | 3/2019 | Morrison |
| 2019/0125697 A1 | 5/2019 | Farfel |
| 2019/0247333 A1 | 8/2019 | Farfel |
| 2019/0308017 A1 | 10/2019 | Edgerton et al. |
| 2019/0380979 A1 | 12/2019 | Galer |
| 2020/0030260 A1 | 1/2020 | Sherrington et al. |
| 2020/0030341 A1 | 1/2020 | Ceulemens |
| 2020/0170965 A1 | 6/2020 | Boyd |
| 2020/0237683 A1 | 7/2020 | Whalley et al. |
| 2020/0261380 A1 | 8/2020 | Abu-Izza |
| 2020/0276136 A1 | 9/2020 | Galer |
| 2020/0297665 A1 | 9/2020 | Martin |
| 2020/0306210 A1 | 10/2020 | Morrison |
| 2020/0330406 A1 | 10/2020 | Galer |
| 2021/0113495 A1 | 4/2021 | Boyd |
| 2021/0121479 A1 | 4/2021 | Ceulemens |
| 2021/0147335 A1 | 5/2021 | Londesbrough |
| 2021/0158920 A1 | 5/2021 | Stewart et al. |
| 2021/0267916 A1 | 9/2021 | Farr |
| 2021/0299064 A1 | 9/2021 | Morrison |
| 2021/0330610 A1 | 10/2021 | Martin |
| 2021/0393550 A1 | 12/2021 | Farr |
| 2021/0401776 A1 | 12/2021 | Martin |
| 2022/0008389 A1 | 1/2022 | Galer |
| 2022/0016053 A1 | 1/2022 | Galer |
| 2022/0096514 A1 | 3/2022 | Quan |
| 2022/0125743 A1 | 4/2022 | Farr |
| 2022/0193082 A1 | 6/2022 | DeWitte et al. |
| 2022/0226262 A1 | 7/2022 | Boyd et al. |
| 2022/0289663 A1 | 9/2022 | Farr |
| 2022/0370381 A1 | 11/2022 | Martin et al. |
| 2023/0076320 A1 | 3/2023 | Martin et al. |
| 2023/0078820 A1 | 3/2023 | Cha et al. |
| 2023/0165810 A1 | 6/2023 | Galer |

FOREIGN PATENT DOCUMENTS

| | | |
|---|---|---|
| CN | 103025301 | 4/2013 |
| CN | 103502245 A | 1/2014 |
| CN | 103886415 | 6/2014 |
| CN | 104800168 | 7/2015 |
| CN | 111971035 | 11/2020 |
| DE | 2150399 | 4/1973 |
| EP | 0 441 160 | 8/1991 |
| EP | 0 810 195 | 12/1997 |

(56) References Cited

FOREIGN PATENT DOCUMENTS

| | | |
|---|---|---|
| EP | 0 920 864 | 6/1999 |
| EP | 1 399 015 | 1/2010 |
| EP | 2 399 513 | 12/2011 |
| EP | 3170807 | 5/2017 |
| FR | 2663539 | 12/1991 |
| GB | 1413078 | 7/1973 |
| GB | 1399015 | 6/1975 |
| GB | 1413070 | 11/1975 |
| GB | 2531282 | 4/2016 |
| GB | 2568809 A | 5/2019 |
| HU | 204497 | 1/1992 |
| JP | A S64-066116 | 3/1989 |
| JP | H05-310564 A | 11/1993 |
| JP | A-2008-536545 | 9/2008 |
| JP | A-2009-525977 | 7/2009 |
| JP | A 2010-520162 | 6/2010 |
| JP | A-2011-221623 | 11/2011 |
| JP | A-2011-529923 | 12/2011 |
| JP | A-2012-511969 | 5/2012 |
| JP | A-2012-520130 | 9/2012 |
| JP | A-2012-208669 | 10/2012 |
| JP | A-2013-536857 | 9/2013 |
| JP | A-2013-248329 | 12/2013 |
| JP | 2016-518387 | 6/2016 |
| JP | 2016 216438 A | 12/2016 |
| JP | 2017-519758 | 7/2017 |
| JP | 2018-525418 | 9/2018 |
| RU | 2317104 | 2/2008 |
| RU | 103209 | 3/2011 |
| RU | 2503448 | 1/2014 |
| RU | 2571501 | 12/2015 |
| WO | WO 1994/018962 | 9/1994 |
| WO | WO 1995/04713 | 2/1995 |
| WO | WO 1995/32962 | 12/1995 |
| WO | WO 2001/86506 | 11/2001 |
| WO | WO 2003/026591 | 4/2003 |
| WO | WO 2003/077847 | 9/2003 |
| WO | WO 2005/004865 | 1/2005 |
| WO | WO 2006/034465 | 3/2006 |
| WO | WO 2006/100676 | 9/2006 |
| WO | WO 2007/034476 | 3/2007 |
| WO | WO 2007/073503 | 6/2007 |
| WO | WO 2007/079181 | 7/2007 |
| WO | WO 2007/092469 | 8/2007 |
| WO | WO 2008/025148 | 3/2008 |
| WO | WO 2008/104524 | 9/2008 |
| WO | WO 2009/087351 | 7/2009 |
| WO | WO 2010/015029 | 2/2010 |
| WO | WO 2010/020585 | 2/2010 |
| WO | WO 2010/025931 | 3/2010 |
| WO | WO 2010/075115 | 7/2010 |
| WO | WO 2010/104841 | 9/2010 |
| WO | WO 2010/121022 | 10/2010 |
| WO | WO 2011/112606 | 9/2011 |
| WO | WO 2011/146850 | 11/2011 |
| WO | WO 2012/030927 | 3/2012 |
| WO | WO 2012/093255 | 7/2012 |
| WO | WO 2012/154812 | 11/2012 |
| WO | WO 2013/096878 | 6/2013 |
| WO | WO 2013/112363 | 8/2013 |
| WO | WO 2013/122897 | 8/2013 |
| WO | WO 2014/177676 | 11/2014 |
| WO | WO 2015/013397 | 1/2015 |
| WO | WO 2015/026849 | 2/2015 |
| WO | WO 2015/066344 | 5/2015 |
| WO | WO 2015/163098 | 10/2015 |
| WO | WO 2015/193668 | 12/2015 |
| WO | WO 2016/051271 | 4/2016 |
| WO | WO 2016/059403 | 4/2016 |
| WO | WO 2016/138138 | 9/2016 |
| WO | WO 2016/205671 | 12/2016 |
| WO | WO 2017/035267 | 3/2017 |
| WO | WO 2017/112702 | 6/2017 |
| WO | WO 2017/122701 | 6/2017 |
| WO | WO 2017/170354 | 10/2017 |
| WO | WO 2018/037306 | 3/2018 |
| WO | WO 2018/060732 | 4/2018 |
| WO | WO 2018/206924 | 11/2018 |
| WO | WO 2019/064031 | 4/2019 |
| WO | WO 2019/067405 | 4/2019 |
| WO | WO 2019/067413 | 4/2019 |
| WO | WO 2019/067419 | 4/2019 |
| WO | WO 2019/204593 | 10/2019 |
| WO | WO 2019/216919 | 11/2019 |
| WO | WO 2019/241005 | 12/2019 |
| WO | WO 2020/014075 | 1/2020 |
| WO | WO 2020/105005 | 5/2020 |
| WO | WO 2020/112460 | 6/2020 |
| WO | WO 2020/176276 | 9/2020 |
| WO | WO 2021/156437 | 8/2021 |
| WO | WO 2022/013425 | 1/2022 |
| WO | WO 2022/069489 | 4/2022 |
| WO | WO 2023/034115 | 3/2023 |
| WO | WO 2023/101866 | 6/2023 |

OTHER PUBLICATIONS

Anonymous, "Determination That PONDIMIN (Fenfluramine Hydrochloride) Tablets, 20 Milligrams and 60 Milligrams, and PONDEREX (Fenfluramine Hydrochloride) Capsules, 20 Milligrams Were Withdrawn From Sale for Reasons of Safety or Effectiveness", Federal Register, (Sep. 29, 2015).

Anonymous, "MacReportMedia—Brabant Pharma Reports Two-Year Follow-up Data From a 19-year Observational Study Using Low-Dose Fenfluramine for the Treatment of Dravet Syndrome", Nov. 25, 2013 (Nov. 25, 2013).

Anonymous, "Health Technology Briefing: Fenfluramine hydrochloride for treatment of seizures associated with Lennox-Gastaut syndrome" NIHR Innovation Observatory (May 2019) 8 pages.

Anonymous "Selective Serotonin reuptake Inhibitor—Wikipedia" Internet https://en.wikipedia.org/wiki/Selective_serotonin_reuptake_inhibitor (Feb. 1, 2020 (retrived on Feb. 4, 2020)).

Anonymous "Zogenix Announces Positive Top-Line Results from Global Pivotal Phase 3 Trial of FINTEPLA for the treatment of Lennox-Gastaut Syndrome" Bio Space (Feb. 6, 2020) pp. 1-12.

Aras et al., "The European patient with Dravet Syndrome: Results from a parent-reported survey on antiepileptic drug use in the European population with Dravet Syndrome" Epilepsy & Behavior (2015) 44:104-109.

Arzimanoglou et al., "Dravet syndrome: From electroclinical characteristics to molecular biology" Epilepsia, 50(Suppl. 8):3-9 (2009).

Bagdy et al., "Serotonin and epilepsy," J. Neurochem., 100:857-73 (2007).

Baker, M. "Zogenix Completes Enrollment in Phase 3 Trial of FINTEPLA in Lennox-Gastaut Syndrome" (Jul. 8, 2019) 2 pages.

Bird et al., "Combination of pharmaceutical compositions for treatment of neurological disorders" STN International (Columbus, Ohio) HCAPLUS database, Accession No. 2013:83254 (2013).

Boel and Casaer, "Add-on Therapy of Fenfluramine in Intractable Self-Induced Epilepsy" Neuropaediatrics 1996, 27(4):171-173.

F Brenot et al., "Primary Pulmonary Hypertension and Fenfluramine Use.", Heart, vol. 70, No. 6, Dec. 1, 1993 (Dec. 1, 1993), pp. 537-541.

Brunklaus et al., "Prognostic, clinical and demographic features in SCN1A mutation-positive Dravet syndrome" Brain, 2012, p. 1-8.

Brunklaus et al., "Dravet syndrome-From epileptic encephalopathy to channelopathy" Epilepsia (May 16, 2014) 55(7):979-984.

Buchanan, Gordon F. et al., Serotonin neurones have anticonvulsant effects and reduce seizure-induced mortality, The Journal of Physiology, 2014, vol. 592, Issue 19, p. 4395-4410.

Carvalho et al., "d-Amphetamine Interaction with Glutathione in Freshly Isolated Rat Hepatocytes" Chemical Research in Toxicology (Jan. 1996) 9(6):1031-1036.

Casaer et al., "Fenfluramine as a Potential Antiepileptic Drug" Epilepsia, 43(2), 205-206, 2002.

C. B. Catarino et al. "Dravet Syndrome as epileptic encephalopathy: Evidence from long-term course and neuropathology", Brain, vol. 134, No. 10 (Jun. 29, 2011) pp. 2982-3010.

(56) References Cited

OTHER PUBLICATIONS

Ceulemans et al., "Poster presented at the 69th Annual Meeting of the American Epilepsy Society" (Dec. 2015) Philadelphia.
Ceulemans et al., "Successful use of fenfluramine as an add-on treatment for Dravet syndrome" Epilepsia, 53(7), 2012, 1131-1139.
Ceulemans, "Overall management of patients with Dravet syndrome" Developmental Medicine & Child Neurology, 2011, 53, 19-23.
Ceulemans B. et al., "Successful use of Fenflurarmine as add-on treatment in Dravet syndrome: a two year prospective follow up", European Journal of Paediatric Neurology, vol. 17, 01101866, Sep. 1, 2013 (Sep. 1, 2013).
Ceulemans B., "Successful Use of Fenfluramine as Add-On Treatment in Dravet Syndrome" Epilepsia, 52(Suppl. 6):4-22 (2011).
Ceulemans et al., "Five-year extended follow-up status of 10 patients with Dravet syndrome treated with fenfluramine" Epilepsia (May 20, 2016) 57(7):e129-e134.
Ceulemans et al., "Clinical Correlations of Mutations in the SCN1A Gene: From Febrile Seizures to Severe Myoclonic Epilepsy in Infancy" Pediatr. Neurol. 30(4):236-43 (2004).
Chiron et. al., "The pharmacologic treatment of Dravet syndrome" Epilepsia (2011) 52(Suppl 2):72-75.
Clemens B., "Dopamine agonist treatment of self-induced pattern-sensitive epilepsy. A case Report" Epilepsy Res. 2. 1988, p. 340-343.
Clinical Trials ClinicalTrials.gov Identifier: NCT02224560 (Jul. 27, 2018).
Coleman et al., "Monitoring for adverse drug reactions," Br. J. Clin. Pharmacol., 61(4):371-78 (2006).
Coma et al., "New combination therapies for treating neurological dissorders" STN International (Columbus, Ohio) HCAPLUS database, Accession No. 2013:682383 (2013).
Cozzi et al., "Indan Analogs of Fenfluramine and Norfenfluramine Have Reduced Neurtoxic Potential" Pharmacology Biochemistry and Behavior (1998) 59(3):709-715.
Curzon et al., "Appetite suppression by commonly used drugs depends on 5-HT receptors but not on 5-HT availability" TIPS (1997) 18:21-25.
Devinsky et al., "Trial of Cannabidiol for Drug-Resistant Seizures in the Dravet Syndrome" The New Engalnd Journal of Medicine (May 25, 2017) 376(21):2011-2020.
"Diacomit: EPAR—Scientific Discussion," European Medicines Agency ("EPAR Diacomit") https://www/ema/europa.eu/en/documents/scientific-discussion/diacomit-epar-scientific-discussion_en.pdf, published 2009.
Dimpfel et al., "Hesperidin and hesperetin for the treatment of epilepsy migraine, schizophrenia, depression, and drug abuse" STN International (Columbus, Ohio) HCAPLUS database, Accession No. 2006:1205690 (2006).
C. Doege et al., "Myoclonic-astatic epilepsy: Doose-Syndrum 2014: Doose syndrome 2014", Zeitschrift FR Epileptologie, (Mar. 20, 2014).
Döring et al. "Thirty Years of Orphan Drug Legislation and the Development of Drugs to Treat Rare Seizure Conditions: A Cross Sectional Analysis" PLOS One, pp. 1-15 (Aug. 24, 2016).
Dravet, Charlotte, "The core Dravet syndrome phenotype" Epilepsia, 52(Supp. 2):3-9 (2011).
Droogmans et al., "Role of echocardiography in tox heart vavulopathy" European Journal of Echocardiography, 10:467-476 (2009).
Experimental Chemistry (Continued), Part 2, Separation and Purification, (Maruzen, Co., Ltd.), Jan. 25, 1967, pp. 159-162 and 184-193.
Faingold et al., "Prevention of seizure-induced sudden death in a chronic SUDEP model by semichronic administration of a selective serotonin reuptake inhibitor" Epilepsy & Behavior (2011) 22:186-190.
Favale et al., "The anticonvulsant effect of citalopram as indirect evidence of serotonergic impairment in human epileptogenesis" Seizure (2003) 12:316-319.
Ferretti et al., "Direct High-performance liquid chromatograph resolution on a chiral column of dexfenfluramine and its impurities, in bulk raw drug and pharmaceutical formulations" J. Chromatogr. A. 731:340-45 (1996).
File History of U.S. Pat. No. 9,549,909 issued on Jan. 24, 2018 (571 pp).
File History of U.S. Pat. No. 9,603,815 issued on Mar. 28, 2017 (385 pp).
File History of U.S. Pat. No. 9,603,814 issued on Mar. 28, 2017 (466 pp).
File History of U.S. Pat. No. 9,610,260 issued on Apr. 4, 2017 (371 pp).
File History of U.S. Pat. No. 10,478,441 issued on Nov. 19, 2019 (761 pp).
File History of U.S. Pat. No. 10,478,442 issued on Nov. 19, 2019 (980 pp).
File History of U.S. Appl. No. 14/447,369, filed Jul. 30, 2014 (now abandoned) (285 pp.).
File History of U.S. Appl. No. 15/429,650, filed Feb. 10, 2017 (now abandoned) (267 pp).
File History of U.S. Appl. No. 15/429,641, filed Feb. 10, 2017 (now abandoned) (285 pp).
File History of U.S. Appl. No. 15/429,506, filed Feb. 10, 2017 (now abandoned) (641 pp).
File History of U.S. Appl. No. 16/596,166, filed Oct. 8, 2019 (now abandoned) (123 pp).
File History of U.S. Appl. No. 16/869,284, filed May 7, 2020 (now abandoned) (42 pp).
File History of U.S. Appl. No. 16/909,055, filed Jun. 12, 2020 (pending) (85 pp).
File History of U.S. Pat. No. 10,351,509 issued Jul. 16, 2019 (226 pp).
File History of U.S. Pat. No. 10,351,510 issued Jul. 16, 2019 (244 pp).
File History of U.S. Pat. No. 10,947,183 issued Mar. 16, 2021 (293 pp).
Franco-Perez, Javier "The Selective Serotonin Reuptake Inhibitors: Antidepressants with Anticonvulsant Effects?" Ann Deoress Anxiety (2014) 1(5):1025 (2 pages).
Garone et al., "Deoxypyrimidine monophosphate bypass therapy for thymidine kinase 2 deficiency" EMBO Molecular Medicine Aug. 1, 2014) 6(8):1016-1027.
Gastaut et al., "Compulsive respiratory sterotypies in children with autistic features: Polygraphic recording and treatment with fenfluramine" Journal of Autism and Developmental Disorders, (Sep. 1, 1987) 17(3):391-406.
K Gentsch et al., "Laboratory Research Fenfluramine Blocks Low-Mg2'-Induced Epileptiform Activity in Rat Entorhinal Cortex" Epilepsia, Jan. 1, 2000 (Jan. 1, 2000), pp. 925-928.
Gharedaghi et al., "The role of different serotonin receptor subtypes in seizure susceptibility" Exp. Brain Res (2014) 232:347-367.
Gioia et al., "Confirmatory Factor Analysis of the Behavior Rating Inventory of Executive Function (BRIEF) in a Clinical Sample" Child Neuropsychology (2002) 8(4):249-57.
Gordon et al., "A SARS-CoV-2 protection interaction map reveals targets for drug repurposing" Nature (Apr. 30, 2020) 583(7816:459-468.
Gross et al., "The influence of the sparteine/debrisoquine genetic polymorphism on the disposition of dexfenfluramine" Br J Clin Pharmacol (1996) 41:311-317.
Habibi et al., "The Impact of Psychoactive Drugs on Seizures and Antiepileptic Drugs" Current Neurology and Neuroscience Reports (Jun. 17, 2016) 16(8):1-10.
Haritos et al., "Metabolism of dexfenfluramine in human liver microsomes and by recombinant enzymes: Role of CYP2D6 and 1A2" Pharmcogenetics (Oct. 1998) 8(5):423-432.
Harvard Health Publishing, Harvard Medical School Generalized Seizures (Grand Mal Seizures) (Apr. 2014) pp. 1-5 (https://www.health.hearvard.edu/diseases-and-conditions/generalized-seizures-grand-mal-se . . . ).
Hattori et al., "A Screening test for the prediction of Dravet Syndrome before one year of age" Epilepsia (Apr. 2008) 49(4):626-633.

(56) References Cited

OTHER PUBLICATIONS

Haute Autorité de Santé (HAS), French National Authority for Health, issued an opinion on Diacomit ("HAS Opinion") https://www.has-sante.fr/upload/dox/application/pdf/2010-01/diacomit_ct_4347.pdf (Jun. 6, 2007).

Hawkins et al., "Synthesis of [14C] Fenfluramine and [14C]-S780" Journal of Labelled Compounds (1974) 10(4):63-670.

Hazai et al., "Reduction of toxic metabolite formation of acetaminophen" Biochemical and Biophysical Research Communications (Mar. 8, 2002) 291(4):1089-1094.

Hegadoren et al., "Interactions of iprindole with fenfluramine metabolism in rat brain and liver" Journal of Psychiatry & Neuroscience (Mar. 1991) pp. 5-11.

Heisler et al., "Epilepsy and Obesity in Serotonin 5-HT$_{2C}$ Receptor Mutant Mice," Ann. NY Acad. Sci. 861:74-78 (1998).

Hirayama, Noriaki, Organic Compound Crystallization Handbook: Principles and Know-How (Maruzen, Co., Ltd.), Jul. 25, 2008, pp. 57-84.

Inoue et al., "Stiripentol open study in Japanese patients with Dravet Syndrome" Epilepsia, 50(11):2362-2368 (2009).

International Conference on Harmonisation of Technical Requirements for Registration of Pharmaceuticals for Human Use, "ICH Harmonised Tripartite Guidline: Impurities in New Drug Substances," Q3A(R2) (2006).

Isaac, Methvin, Serotonergic 5-HT2C Receptors as a Potential Therapeutic Target for the Design Antiepileptic Drugs, Current Topics in Medicinal Chemistry, 2005, vol. 5, Issue 1, p. 59-67.

Ji et al., "Study of Fenfluramine Synthesis Route" Journal of Shenyang College of Pharmacy (Apr. 1994) 11(2):116-118.

Jingyu et al., "Study on Synthesis of Amphetamine Compounds" Chem J. of Chinese Univ., 9(2), 12 pages (1988).

Kaiser et al., "Synthesis and Anorectic Activity o Some 1-Benzylcyclopropylamines" Journal of Medicinal Chemistry, American Chemical Society, US (1970) 13(5):820-826.

Katholieke Universiteit Leuven, University Hospital Antwerp: "Interim results of a fenfluramine open-label extension study", European Patent Register (May 25, 2017).

Kelley et al., "Doose syndrome (myoclonic-astatic epilepsy): 40 years of progress" Developmental Medicine & Child Neurology (2010) 52(11):988-993.

Klein et al., "Cannabidiol potentiates Delta$^9$-tetrahydrocannabinol (THC) behavioural effects and alters THC pharmacokinetics during acute and chronic treatment in adolescent rats" Psychopharmacology (2011) 218:443-457.

Klein, M. T. and Teitler, M. , Distribution of 5-htlE receptors in the mammalian brain and cerebral vasculature: an immunohistochemical and pharmacological study, British Journal of Pharmacology, Jun. 2012, vol. 166, No. 4, p. 1290-1302.

Lagae et al. "A pilot, open-label study of the effectiveness and tolerability of low-dose ZX008 (fenfluramine HCl) in Lennox-Gastaut syndrome" Epilepsia (2018) 59: 1881-1888.

Lambert et al., "Inductive Enhancement of Aryl Participation" Journal of the American Chemical Society (Apr. 27, 1977) 99(9):3059-67.

Leit, Silvana et al., Design and synthesis of tryptamine-based 5HT2C agonists for the treatment of certain CNS disorders, Division of Medicinal Chemistry Scientific Abstracts for the 240th National ACS Meeting and Exposition, Jul. 28, 2010, MEDI367.

LeJeune et al., "Psychometric Support for an Abbreviated Version of the Behavior Rating Inventory of Executive Function (BRIEF) Parent Form" Child Neuropsychology (2010 16:182-201.

Lewis et al., "Biosynthesis of Canescin, a Metabolite of *Aspergillus malignus*: Incorporation of Methionine, Acetate, Succinate, and Isocoumarin Precursors, Labelled with Deuterium and Carbon-13" J. Chem. Soc. Perkin Trans I (1988) pp. 747-754.

Lopez-Meraz et al., "5-HT$_{1A}$ receptor agonist modify epileptic seizures in three experimental models in rats" Neuropharmacology (2005) 49:367-375.

Lopinto-Khoury et al., "Antiepileptic Drugs and Markers of Vascular Risk" Curr Treat Options Neurol (Jul. 2010) 12(4):300-308.

Manzke et al., "5-HT4(a) receptors avert opiod-induced breathing depression without loss of analgesia" Science (Jul. 11, 2003) 301:226-229.

Martin, et al., "An Examination of the Mechanism of Action of Fenfluramine in Dravet Syndrome: A Look Beyond Serotonin" Presented as part of the Zogenix Scientific Exhibit During the 70$^{th}$ Annual Meeting of the American Epilepsy Society, Houston, Texas (Dec. 2-6, 2016).

Martin et al., "Fenfluramine acts as a positive modulator of sigma-1 receptors" Epilepsy and Behavior, Academic Press, San Diego, CA, US (Mar. 10, 2020) 105:1-9.

Mathews et al., "Effect of D-Fenfluramine on the Lymphocyte Response of HIV+ Humans" International Journal of Immunopharmacology (Jan. 1, 1998) 20:751-763.

McTague et al., "The genetic landscape of the epileptic encephalopathies of infancy and childhood" Lancet Neurol. (2016) 15:304-316.

Meador K J., "Seizure reduction with fluoxetin in an adult woman with Dravet syndrome", Epilepsy & Behavior Case Reports, Elsevier BV, NL, vol. 2, Jan. 1, 2014 (Jan. 1, 2014), pp. 54-56.

Mudigoudar et al., "Emerging Antiepileptic Drugs for Severe Pediatric Epilepsies" Seminars in Pediatric Neurology (Jun. 2016) 23(2):167-179.

Mulley et al., "SCN1A Mutations and Epilepsy" Human Mutation (2005) 25:535-542.

Naithani et al., "The Conventional Antiepileptic Drug Use When Compared to a Combination Therapy Regime in a Teaching Hospital in India" International Journal of Pharma and Bio Sciences (2012) 3(1):B-191-B-197.

NCT02682927 (Sep. 3, 2016, 10 pages) Accessed from https://www.clinicaltrials.gov/ct2/history/NCT02682927?V_=View#StudyPageTop on Mar. 18, 2019).

Notification issued by the Director of Pharmaceutical and Medical Safety Bureau, Ministry of Health and Welfare, Guidelines for Residual Solvents in Pharmaceuticals, PMSB/ELD Notification No. 307, 1998, pp. 1-11.

Nozulak et al., "(+)-cis-4,5,7a,8,9,10,11,11a-Octahydro-7H-10-methylindolo[1,7-bc][2,6]-naphthridine: A 5-HT$_{2C/2B}$ Receptor Antagonist with Low 5-HT$_{2A}$ Receptor Affinity" J. Med. Chem. (1995) 38:28-33.

Oguni et al., "Treatment and Long-Term Prognosis of Myoclonic-Astatic Epilepsy of Early Childhood," Neuropediatrics (2002) 33(3):122-32.

Olson et al., "Cyclin-Dependent Kinase-Like 5 Deficiency Disorder: Clinical Review" Pediatric Neurology (2019) 97:18-25.

O'Neill et al., "GR46611 potentiates 5-HT$_{1A}$ receptor-mediated locomotor activity in the guinea pig" European Journal of Pharmacology (1999) 370:85-92.

ONFI Prescribing Information. Lundbeck, Deerfield, Reference ID: 4028780 [online], Dec. 2016, [retrieved on Jun. 22, 2021, <URL: https://www.accessdata.fda.gov/drugsatfda_docs/label/2016/203993s005lbl.pdf>.

Patani et al;, "Bioisosterism: A Rational Approach to Drug Design" Chem. Rev. (1996) 96:3147-3176.

Pirincci et al., "The Effects of Fefluramine on Blood and Tissue Seratonin (5- Hydroxytryptamine) Levels in Rats" Turk J Vet Anim Sci (2005) 29:857-863.

Pittala, Valeria et al., 5-HT7 Receptor Ligands: Recent Developments and Potential Therapeutic Applications, Mini-Reviews in Medicinal Chemistry, 2007, vol. 7, Issue 9, p. 945-960.

Porra et al., "Determination of Fenfluramine Enantiomers in Pharmaceutical Formulations by Capillary Zone Electrophoresis" Chromatographia (Oct. 1995) 41(7/8):383-388.

Pottkamper et al., "The postictal state—What do we know?" Epilepsia (2020) 61(6):1045-1061.

Public Law 110-85, 110$^{th}$ Congress ("FDA Amendments Act of 2007") published 2007.

Registry(STN) [online], Jun. 7, 2015, [Retrieval Date: Sep. 28, 2020], CAS Registry No. 1775169-27-1.

Jake Remaly: "Fenfluramine Reduces Convulsive Seizure Frequency in Dravet Syndrome. Epilepsy Resource Center", Jan. 1, 2018 (Jan. 1, 2018).

Remi et al., "Clinical features of the postictal state: Correlation with seizure variables" Epilepsy & Behavior (2010) 91(2):114-117.

(56) References Cited

OTHER PUBLICATIONS

Remington, "The Science and Practice of Pharmacy", Nineteenth Edition (1995), pp. 710-712.
Rho, Jong M. "Basic Science Behind the Catastrophic Epilepsies" Epilepsia (2004) 45(Suppl. 5):5-11.
Rothman et al., "(+)-Fenfluramine and Its Major Metabolite, (+)-Norfenfluramine, Are Potent Substrates for Norepinephrine Transporters," J. Pharmacol. Exp. Ther., 305(3):1191-99 (2003).
Rothman et al., "Serotonergic drugs and valvular heart disease" Expert Opinion on Drug Safety (May 2009) 8(3):317-329.
Russo et al., "Agonistic Properties of Cannabidiol at 5-HT1a Receptors" Neurochemical Research (2005) 30(8):1037-1043.
Scala et al., "CDKL5/STK9 is mutated in Rett syndrome variant with infantile spasms" J Med Genet (2005) 42:103-107.
Schoonjans, An-Sofie "Low-dose fenfluramine in the treatment of neurologic disorders: experience in Dravet syndrome" Therapeutic Advances in Neurological Disorders (Jan. 1, 2015) pp. 328-338.
Schoonjans et al. "Low-dose fenfluramine significantly reduces seizure frequency in Dravet syndrome: a prospective study of a new cohort of patients", European Journal of Neurology, vol. 24, No. 2, (Oct. 28, 2016), pp. 309-314.
An-Sofie Schoonjans et al: "Cardiovascular Safety of Low-Dose Fenfluramine in Dravet Syndrome: A Review of its Benefit-Risk Profile in a New Patient Population", Current Medical Research and Opinion, vol. 33, No. 10, Jul. 31, 2017 (Jul. 31, 2017), pp. 1773-1781.
Selmer et al., "SCN1A mutation screening in adult patients with Lenox-Gastaut syndrome features" Epilepsy & Behavior (Nov. 1, 2009) 16(3):555-57.
Sharma et al. Indian Journal of Pharmacology, 1996, 28(1), 1-10.
Slick et al., "Frequency of Scale Elevations and Factor Structure of the Behavior Rating Inventory of Executive Function (Brief) in Children and Adolescents with Intractiable Epilepsy" Child Neuropsychology (2006) 12:181-189.
Sourbron et al., "Serotonergic Modulation as Effective Treatment for Dravet Syndrome in Zebrafish Mutant Model" ACS Chemical Neuroscience (Feb. 17, 2016) 7(5):588-598.
Study NCT02926898 on Date: May 1, 2017 (v6), ClinicalTrials.gov archive[online], May 1, 2017, [retrieved on Jun. 22, 2021], <URL: https://clinicaltrials.gov/ct2/history/NCT02926898>.
Su et al, "The Synthesis of 2-Amino-1-Penylpropanes" Chemical Journal of Chinese Universities (1988) 9(2):134-139.
Subota et al., "Signs and Symptoms of the postictal period in epilepsy: A systematic review and meta-analysis" Epilepsy & Behavior (2019) 94:243-251.
Sullivan et al. "Effect of ZX008 (fenfluramine HCl oral solution) on total seizures in Dravet syndrome" Neurology: Official Journal of the American Academy of Neurology, 2018, 90(24):e2187-e2811.
Thurman et al., "Sudden expected death in epilepsy: Assessing the public health burden" Epilepsia (2014) 55(10):1479-1485.
Tran et al., "Dakin-West Synthesis of β-Aryl Ketones" J. Org. Chem. (2006) 71:6640-6643.
Tupal et al., "Serotonin 5-HT$_4$ receptors play a critical role in the action of fenfluramine to block seizure-induced sudden death in a mouse model of SUDEP" Epilepsy Research (2021) 177:1-7.
Van Der Steldt et al., "The Effect of Alkyl Substitution in Drugs" Arzneimittelforschung—Drug Research (1965) 15:1251-1253.
Van Rijckevorsel, Kenou, "Treatment of Lennox-Gastaut syndrome: overview and recent findings" Neuropsychiatric Disease and Treatment, 4(6):1001-1019 (2008).
Vela, Jose Miguel "Repurposing Sigma-1 Receptor Ligands for COVID-19 Therapy?" Frontiers in Pharmacology (Nov. 9, 2020) 11:1-23.
Vickers et al., "Oral Administration of the 5-HT2C receptor agonist, mCPP, reduces body weight gain in rats over 28 days as a result of maintained hypophagia" Psychopharmacology (May 2003), 167 (3): 274-280.
Viola et al., "The Behavior Rating Inventory of Executive Function (BRIEF) to Identify Pediatric Acute Lymphoblastic Leukemia (ALL) Survivors at Risk for Neurocognitive Impairment" Journal of Pediatric Hematology/Oncology (Apr. 1, 2017) 39(3):174-178.
Vivero et al., "A close look at fenfluramine and dexfenfluramine" The Journal of Emergency Medicine (1998) 16(2):197-205.
Wallace et al., "Pharmacotherapy for Dravet Syndrome" Paediatr. Drugs, 18(3):197-208 (Jun. 2016).
Wee et al., "Risk for Valvular Heart Disease among Users of Fenfluramine and Dexfenfluramine Who Underwent Echocardiography before Use of Medication," Annals of Internal Medicine, 129(11):870-874 (1998).
Werbel et al., "Synthesis, Antimalarial Activity, and Quantitative Structure-Activity Relationships of Tebuquine and a Series of Related 5-[(7-Chloro-4-quinolinyl)amino]-3[(alkylamino)methyl][1,1'-biphenyl]-2-ols and N omega-Oxides" J. Med. Chem. (1986) 29:924-939.
Wirrell et al., "Stiripentol in Dravet syndrome: Results of a retrospective U.S. study" Epilepsia (2013) 54(9):1595-1604.
Wirrell et al., "Stiripentol in Dravet Syndrome: Is it Worth It?" Epilepsy Currents, 14(1):22-23 (Jan./Feb. 2014).
Wirrell et al., "Treatment of Dravet Syndrome" Can. J. Neurol. Sci., 43(Suppl. 3):S13-18 (Jun. 2016).
Wirrell et al., "Optimizing the Diagnosis and Management of Dravet Syndrome: Recommendations From a North American Consensus Panel" Pediatric Neurology (Mar. 2017) 68:18-34.
Wurtman et al., "Fenfluramine and other serotoninergic drugs depress food intake and carbohydrate consumption while sparing protein consumption" Current Medical Research and Opinion (1979) 6(1 Supp):28-33.
Yamaori et al., "Potent inhibition of human cytochrome P450 3A isoforms by cannabidiol: Role of phenolic hydroxyl groups in the resorcinol moiety" Life Sciences (2011) 88:730-736.
Yoshida et al. (2017), "Impact of Physiologically Based Pharmacokinetic Models on Regulatory Reviews and Product Labels: Frequent Utilization in the Field of Oncology" in Clinical Pharmacology and Therapeutics 2017; 101(5): 597-602.
Zaccara et al., "Interactions between antiepileptic drugs, and between antiepileptic drugs and other drugs" Seminar in Epileptology (2014) 16(4):409-432.
Zhang et al., *A Physiological-based Pharmacokinetic (PBPK) Modeling Approach to Quantifying Drug-Drug Interactions: Applications to the Development of Fenfluramine (ZX008) for Treatment of Seizures in Dravet Syndrome (DS)*. Presented at the 2016 American Conference for Pharmacokinetics.
Zhang et al., A Physiological-based Pharmacokinetic (PBPK) Modeling Approach to Quantifying Drug-Drug Interactions: Applications to the Development of Fenfluramine (ZX008) for Treatment of Seizures in Dravet Syndrome (DS). Published in Abstracts accepted for American Conference on Pharmacometrics 2016 (ACoP7).
Zhang et al., "Pharmacological Characterization of an Antisense Knockdown Zebrafish Model of Dravet Syndrome: Inhibition of Epileptic Seizures by the Serotonin Agonist Fenfluramine" PLOS ONE (May 12, 2015) 10(5)::16-17 (Abstract).
Zhuang et al. (2016), "PBPK modeling and simulation in drug research and development" in Acta Pharmaceutica Sinica B 2016;6(5):430-440.
Zogenix "Corporate Update Nasdaq: ZGNX" (Jun. 1, 2016) Retrieved from the Internet: URL:http://www.jefferies.com/CMSFiles/Jefferies.com/files/Conferences/060716/Presentations/Zogenix%20Inc.pdf [retrieved on Feb. 21, 2018].
Asatryan, Babken "Challenges in Decoding Sudden Unexpected Death in Epilepsy: The Intersection Between Heart and Brain in Epilepsy" Journal of the American Heart Association (2021) 10(23):e023571, pp. 1-4.
BNF 39—British National Formulary (Mar. 2000) p. 197.
Caraballo et al., "Ketogenic diet in patients with Lennox-Gastaut syndrome" Seizure (2014) 23:751-755.
Cross et al., "Expert Opinion on the Management of Lennox-Gastaut Syndrome: Treatment Algorithms and Practical Considerations" Frontiers in Neurology (Sep. 29, 2017) 8(505):1-18.
Fisher et al., "Definition of the postictal state: When does it start and End?" Epilepsy & Behavior (2010) 19(2):100-104.

(56) References Cited

OTHER PUBLICATIONS

Grosso et al., "Dexfenfluramine effective in drug-resistant temporal lobe epilepsy" Neurology, Lippincott Williams & Wilkins, Philadelphia, US (Sep. 25, 2001) 57(6):1139-1140.
Hay et al., "Clinical development success rates for investigational drugs" Nature Biotechnology (Jan. 2014) 32(1):40-51.
Knupp et al., "Efficacy and Safety of Fenfluramine for the Treatment of Seizures Associated with Lennox-Gastaut Syndrome" JAMA Neurology (Jun. 2022) 79(6):554-564.
MIMS—Monthly Index of Medical Specialties (Sep. 1997) pp. 240-241.
Samanta, Debopam "Changing Landscape of Dravet Syndrome Management: An Overview" Neuropediatrics (2020) 51(2):135-145.
Anderson et al., "Spreading Depression: Imaging and Blockade in the Rat Neocortical Brain Slice," Journal of Neurophysiology 88(5):2713-3725 (Nov. 1, 2002).
Chiron, "Stiripentol for the treatment of Dravet syndrome" Orphan Drugs: Research and Reviews (2014) 4:29-38.
Ning et al., "Fenfluramine Directly Inhibits Cortical Spreading Depolarization—A Pathophysiologic Process Linked to SUDEP," American Epilepsy Society, pp. 1-3 (Nov. 11, 2021).
Devinsky et al., "Effect of fenfluramine on convulsive seizures in CDKL5 deficiency disorder" Epilepsia (2021) 61(7):E98-E102.
Faingold et al., "Serotonergic agents act on 5-HT3 receptors in the brain to block seizure-induced respiratory arrest in the DBA/1 mouse model of SUDEP" Epilepsy & Behavior (2016) 64:166-170.
Tupal et al., "Prophylaxis of Seizure-Induced Respiratory Arrest (S-IRA) with Fenfluramine in a Mouse Model of SUDEP" 71st American Epilepsy Society Meeting (Nov. 20, 2017) (1 page).
Wang et al., "Neurophysiologic Studies and MRI in Pelizaeus-Merzbacher Disease: Comparison of Classic and Connatal Form" Pediatr. Neurol. (1995) 12:47-53.
DeVane et al., "Dosage Regimen Design" Pharmacology & Therapeutics (1982) 17(2):143-163.
Dominguez-Gonzalez et al., "Deoxynucleoside Therapy for Thymidine Kinase 2-Deficient Myopathy" Annals of Neurology (2019) 86(2):293-303.
Archer et al., "Primary Pulmonary Hypertension, A Vascular Biology and Translational Research "Work in Progress"" Clinical Cardiology: New Frontiers, Circulation, 102:2781-2791 (Nov. 28, 2000).
Echocardiogram, Echocardiogram Test for Pulmonary Arterial Hypertension PAH (https://pulmonaryhypertensionm.com/echocardiogram/) pp. 1-5 (Jan. 4, 2012).
FDA-approved Treatments for Pulmonary Hypertension, Vera Moulton Wall Center for Pulmonary Vascular Diseases, Stanford (https://med.stanford.edu/wallcenter/patient-resources/fda.html) pp. 1-8 (Jan. 19, 2017).
Gardner, Amanda "Living Your Best With Pulmonary Hypertension" WebMD, pp. 1-5 (Jan. 2, 2019).
Khan et al., "Epileptic Encephalopathies: An Overview" Epilepsy Research and Treatment, vol. 2012, pp. 1-8 (Sep. 12, 2012).
Mari et al., "CDKL5 belongs to the same molecular pathway of MeCP2 and it is responsible for the early-onset seizure variant of Rett syndrome" Human Molecular Genetics (2005) 14(14):1935-1946.
Pulmonary Hypertension and Edema, (pulmonaryhypertensionnews.com/pulmonary-hypertension-and-edema/) pp. 1-3 (Nov. 9, 2015).
Scheffer et al., "ILAE classification of the epilepsies: Position paper of the ILAE Commission for Classification and Terminology" Epilepsia (2017) 58)4):512-521.
Specchio et al., "International League Against Epilepsy classification and definition of epilepsy syndromes with onset in childhood: Position paper by the ILAE Task Force on Nosology and Definitions" Epilepsia (Mar. 17, 2022) 00:1-45.
Weir et al., "Anorexic Agents Aminorex, Fenfluramine, and Dexfenfluramine Inhibit Potassium Current in Rat Pulmonary Vascular Smooth Muscle and Cause Pulmonary Vasoconstriction" American Heart Association, Circulation, 94(9):2216-2220 (Nov. 1996).
Zuberi et al., "Commentary: A New Classification is Born" International League Against Epilepsy (2017) pp. 511.
Bishop et al., "Fenfluramine treatment is associated with improvement in everyday executive function in preschool-aged children (<5 years) with Dravet syndrome: A critical period for early neurodevelopment," Epilepsy & Behavior (2023) 138:108994.
Brandt et l., "Cognitive adverse events of topiramate in patients with epilepsy and intellectual disability" Epilepsy & Behavior (2015) 45:261-264.
Chiron, "Stiripentol," Expert Opinion of Investigational Drugs, Informa Healthcare, UK (Jul. 1, 2005) 14(7):904-911.
Devinsky et al., "Sudden expected death in epilepsy: epidemiology, mechanisms and prevention," The Lancet Neurology, (2016) 15(10):1075-1088.
Maiman et al., "Utility of the Behavior Rating Inventory of Executive Function—Preschool version (BRIEF-P) in young children with epilepsy" Child Neuropsychology (2017)24(7):975-985.
Park et al., "Long-Term cognitive and mood effects of zonisamide monotherapy in epilepsy patients" Epilepsy & Behavior (2008) 12:102-108.
Schoonjans et al. "fenfluramine significantly reduces seizure frequency in Dravet syndrome: a prospective study of a new cohort of patients", European Journal of Neurology, (Sep. 11, 2016), p. 1-1.
Strzelczyk et al., "Psychobehavioural and Cognitive Adverse Events of Anti-Seizure Medications for the Treatment of Developmental and Epileptic Encephalopathies" CNS Drugs (2002) pp. 1-33.
Aylward et al., "Screening and Assessment Tools" Developmental-Behavioral Pediatrics Evidence and Practice (2008) 123-201.
Berge et al., "Pharmaceutical Salts" J. Pharm Sci (1977) 68(1):1-19.
Busner et al., "Global Impressions Scale: Applying a Research Tool in Clinical Practice" Psychiatry (2007) 29-37.
Ceulemans B., "Successful Use of Fenfluramine as Add-On Treatment in Dravet Syndrome" Epilepsia, 52(Suppl. 6):4-22 (2011) (Abstract Only).
De Jonghe et al., "Molecular genetics of Dravet syndrome" Developmental Medicine & Child Neurology (2011) 53 (Supp 2):7-10.
Dravet. Charlotte, "Dravet Syndrome History" Developmental Medicine & Child Neurology (2011) 53 (Suppl. 2):1-6.
"Guideline on clinical investigation of medicinal products in the treatment of epileptic disorders" European Medicines Agency (Jul. 22, 2010) pp. 1-17.
Marini et al., "The genetics of Dravet Syndrome" Epilepsia (2011) 52(Suppl. 2):24-29.
Mayer et al., "Refractory Status Epilepticus" Archives of Neurology, American Medial Association, Chicago, Il, US (Feb. 1, 2022) 59(2):205-210.
Patino et al., "A Functional Null Mutation of SCN1B in a Patient with Dravet Syndrome" J. Neurosci. (2009) 29(34):10764-10778.
Rawson et al., "Bacterial and Funcal Coinfection in Individuals with Coronavirus: A Rapid Review to Support COVID-19 Antimicrobial Prescribing" Clinical Infection Diseases (2020) 71:2459-2468.
Shorvon et al., "The treatment of super-refractory status epilepticus: a critical review of available therapies and a clinical treatment protocol" Brain (Oct. 1, 2011) 134(10)2802-2818.
Singh et al., "A Role of SCN9A in Human Epilepsies, as a Cause of Febrile Seizures and as a Potential Modifier of Dravet Syndrome" PLoS Genetics (2009) 5(9):9-12 (pp. 1-14).
Wikipedia "Marburg acute multiple sclerosis" (Dec. 26, 2020), retrieved on Oct. 9, 2022.
Bewernitz et al., "Electroencephalogram-based pharmacodynamic measures: a review." Int J Clin Pharmacol Ther (2012) 50(3):162-84.
Gursoy et al., "Diagnostic Approach to Genetic Causes of Early-Onset Epileptic Encephalopathy," Journal of Child Neurology (2016) 31:523-532.
Karceski et al., "Initial treatment of epilepsy in adults." UptoDate. Retrieved from the WayBackMachine on Sep. 21, 2023, https://web/archive.org/web/20210624202606/https://www.uptodate.com/contents/initial-treatment-of-epilepsy-in-adults. Published Jun. 24, 2021.

(56) References Cited

OTHER PUBLICATIONS

Mayhew et al., "Moving towards meaningful measurement: Rasch analysis of the Morth Start Ambulatory Assessment in Duchenne muscular dystrophy" Developmental Medicine & Child Neurology (2011) 53:535-542.

Naegelin et al., "OP24-2321 FINEORETT—An ongoing phase I clinical study to assess safety and efficacy of oral fingolimod (FTY720) in children with Rett syndrome" European Journal of Paediatric Neurology (May 22, 2015) 19:58.

Tatum et al., "Clinical utility of EEG in diagnosing and monitoring epilepsy in adults." Clinical Neurophys. (2018) 129(5):1056-1082.

Abraham et al., "Relationship of Childhood Weight Status to Morbidity in Adults," HSMHA Health Reports (1971) 86:273-284.

Bialer et al., "Progress report on new antiepileptic drugs: A Summary of the Thirteenth Eilat Conerence on New Antiepileptic Drugs and Devices (EILAT XIII)" Epilepsia (2017) 58(2):181-221.

Campbell et al., "Plasma concentrations of fenfluramine and its metabolite, nonfenfluramine, after single and repeated oral administration," Br. J. Pharmacol. (1971) 43:465-466.

Journal of the Japanese Society of Internatil Medine (2011) 100(2):426-431.

Karussis, "The Diagnosis of multiple sclerosis and the various related demyelinating syndromes A critical review," Journal of Autoimmunity (2014) 48:134-142.

Landmark et al., "Drug interactions involving the new second- and third-generation antiepileptic drugs" Exprt Rev. Neurother. (2010) 20(1):119-140.

Mangatt et al., "Prevalence and onset of comorbidities in the CDKL5 disorder differ from Rett syndrome" Orphanet Journal of Rare Diseases (2016) 2:1-17.

Nickels et al., "Stiripentol in the Management of Epilepsy" CNS Drugs (2017) 31:405-416.

METHOD FOR THE TREATMENT OF DRAVET SYNDROME

BACKGROUND ART

This invention relates to the treatment of Dravet Syndrome using an amphetamine derivative, specifically fenfluramine.

Fenfluramine, i.e. 3-trifluoromethyl-N-ethylamphetamine is an amphetamine derivative having the structure:

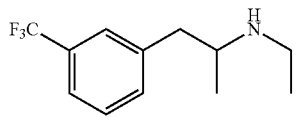

Fenfluramine was first marketed in the US in 1973 and had been administered in combination with phentermine to prevent and treat obesity. However, in 1997, it was withdrawn from the US market as its use was associated with the onset of cardiac fibrosis and pulmonary hypertension. Subsequently, the drug was withdrawn from sale globally and is no longer indicated for use in any therapeutic area.

Despite the health concerns surrounding fenfluramine, attempts have been made to identify further therapeutic uses for that product. Aicardi and Gastaut (*New England Journal of Medicine* (1985), 313:1419 and *Archives of Neurology* (1988) 45:923-925) reported four cases of self-induced photosensitive seizures that responded to treatment with fenfluramine.

Clemens, in *Epilepsy Research* (1988) 2:340-343 reported a study on a boy suffering pattern sensitivity-induced seizures that were resistant to anticonvulsive treatment. Fenfluramine reportedly successfully terminated these self-induced seizures and the author concluded that this was because fenfluramine blocked the photosensitive triggering mechanism.

In *Neuropaediatrics*, (1996); 27(4):171-173, Boel and Casaer reported on a study on the effects of fenfluramine on children with refractory epilepsy. They concluded that when fenfluramine was administered at a dose of 0.5 to 1 mg/kg/day, this resulted in a reduction in the number of seizures experienced by the patients.

In a letter to Epilepsia, published in that journal (*Epilepsia*, 43(2):205-206, 2002), Boel and Casaer commented that fenfluramine appeared to be of therapeutic benefit in patients with intractable epilepsy.

Epilepsy is a condition of the brain marked by a susceptibility to recurrent seizures. There are numerous causes of epilepsy including, but not limited to birth trauma, perinatal infection, anoxia, infectious diseases, ingestion of toxins, tumours of the brain, inherited disorders or degenerative disease, head injury or trauma, metabolic disorders, cerebrovascular accident and alcohol withdrawal.

There are a large number of subtypes of epilepsy that have been characterised. For example, the following list of conditions are set out in *Meritt's Neurology* (12th Edition):
I. Idiopathic epilepsy syndromes (focal or generalised)
   A. Benign neonatal convulsions
     1. Familial
     2. Nonfamilial
   B. Benign childhood epilepsy
     1. With central-midtemporal spikes
     2. With occipital spikes
   C. Childhood/juvenile absence epilepsy
     Juvenile myoclonic epilepsy (including generalised tonic-clonic seizures on awakening)
   E. Idiopathic epilepsy, otherwise unspecified
II. Symptomatic epilepsy syndromes (focal or generalised)
   A. West syndrome (infantile spasms)
   B. Lennox-Gastaut syndrome
   C. Early myoclonic encephalopathy
   D. Epilepsia partialis continua
   1. Rasmussen syndrome (encephalitic form)
   2. Restricted form
   E. Acquired epileptic aphasia (Landau-Kleffner syndrome)
   F. Temporal lobe epilepsy
   G. Frontal lobe epilepsy
   H. Posttraumatic epilepsy
   I. Other symptomatic epilepsy, focal or generalised, not specified
III. Other epilepsy syndromes of uncertain or mixed classification
   A. Neonatal seizures
   B. Febrile seizures
   C. Reflex epilepsy
   D. Other unspecified As can be seen from, for example, Part III of that list, there are still subtypes of epilepsy that have not yet been fully characterised and thus, the list is far from complete.

Those skilled in the art will recognize that these subtypes of epilepsy are triggered by different stimuli, are controlled by different biological pathways and have different causes, whether genetic or environmental. In other words, the skilled artisan will recognize that teachings relating to one epileptic subtype are not necessarily be applicable to other subtypes. This can include recognition that different epilepsy subtypes respond differently to different anticonvulsant drugs.

Dravet Syndrome is a rare and catastrophic form of intractable epilepsy that begins in infancy. Initially, the patient experiences prolonged seizures. In their second year, additional types of seizure begin to occur and this typically coincides with a developmental decline, possibly due to repeated cerebral hypoxia. This leads to poor development of language and motor skills.

Children with Dravet Syndrome are likely to experience multiple seizures per day. Epileptic seizures are far more likely to result in death in sufferers of Dravet Syndrome; approximately 10 to 15% of patients diagnosed with Dravet Syndrome die in childhood, particularly between two and four years of age. Additionally, patients are at risk of numerous associated conditions including orthopedic developmental issues, impaired growth and chronic infections.

Of particular concern, children with Dravet Syndrome are particularly susceptible to episodes of *Status Epilepicus*. This severe and intractable condition is categorized as a medical emergency requiring immediate medical intervention, typically involving hosptialisation. *Status Epilepticus* can be fatal. It can also be associated with cerebral hypoxia, possibly leading to damage to brain tissue. Frequent hospitalizations of children with Dravet Syndrome are clearly distressing, not only to the patient but also to family and carers.

The cost of care for Dravet Syndrome patients is also high as the affected children require constant supervision and many require institutionalisation as they reach teenage years.

At present, although a number of anticonvulsant therapies can be employed to reduce the instance of seizures in patients with Dravet Syndrome, the results obtained with such therapies are typically poor and those therapies only effect partial cessation of seizures at best.

Seizures associated with Dravet Syndrome are typically resistant to conventional treatments. Further, many anticonvulsants such as clobazam and clonazepam have undesirable side effects, which are particularly acute in pediatric patients.

Stiripentol is approved in Europe but not in the US for the treatment of Dravet Syndrome. It does not exhibit an anticonvulsant activity in its own right; it acts by inhibiting the metabolism of other anticonvulsants thereby prolonging their activity. However, concerns remain regarding the use of stiripentol due to its inhibitory effect on hepatic cytochrome P450. Further, the interactions of stiripentol with a large number of drugs means that combination therapy (which is typically required for patients with Dravet Syndrome) is problematic.

There is accordingly a need to provide an improved method for treating or preventing Dravet Syndrome and I or for treating, preventing and/or ameliorating seizures experienced by sufferers of Dravet Syndrome.

BRIEF SUMMARY OF THE INVENTION

According to a first aspect of the present invention, there is provided a method of treating and/or preventing Dravet Syndrome in a patient comprising administering an effective dose of fenfluramine to that patient.

According to a further aspect of the present invention, there is provided a method of treating, preventing and/or ameliorating seizures in a patient diagnosed with Dravet Syndrome comprising administering an effective dose of fenfluramine to that patient.

According to a further aspect of the present invention, there is provided a method of treating a patient that exhibits a mutation in one or more of a gene selected from the group consisting of SCN1A, SCN1B, SCN2A, SCN3A, SCN9A, GABRG2, GABRD and PCDH19 by by administering to that patient an effective dose of fenfluramine.

A still further aspect of this invention contemplates a method for stimulating one or more 5-HT receptors in the brain of a patient by administering an effective dose of fenfluramine or a pharmaceutically acceptable salt thereof to that patient. Illustrative one or more 5-HT receptors are selected from the group consisting of one or more of $5\text{-HT}_1$, $5\text{-HT}_{1A}$, $5\text{-HT}_{1B}$, $5\text{-HT}_{1C}$, $5\text{-HT}_{1D}$, $5\text{-HT}_{1E}$, $5\text{-HT}_{1F}$, $5\text{-HT}_2$, $5\text{-HT}_{2A}$, $5\text{-HT}_{2B}$, $5\text{-HT}_{2C}$, $5\text{-HT}_3$, $5\text{-HT}_4$, $5\text{-HT}_5$, $5\text{-HT}_{5A}$, $5\text{-HT}_{5B}$, $5\text{-HT}_6$, and $5\text{-HT}_7$.

Yet another aspect of the invention contemplates coadministration of an effective dose of one or more co-therapeutic agents with the fenfluramine.

DETAILED DESCRIPTION OF THE INVENTION

After many years of extensive research, it has unexpectedly been found that fenfluramine can be used to treat, or at least minimiZe the effects of Dravet Syndrome. This is confirmed by the results presented herein, and also in the article by Ceulemans et al., *Epilepsia* (2012) 53(7):1131-1139, the contents of which are incorporated herein.

For the avoidance of doubt, the term "prevention" of seizures means the total or partial prevention (inhibition) of seizures. Ideally, the methods of the present invention result in a total prevention of seizures; indeed, this ideal has been achieved in a number of patients treated by the inventors. However, the invention also encompasses methods in which the instances of seizures are decreased by at least 50%, at least 60%, at least 70%, at least 80% or at least 90%.

It is known that patients with Dravet Syndrome commonly experience photosensitive or induced seizures. From teachings in the prior art, e.g. Aicardi and Gastaut (1988) and Boel and Casaer (1996)—both discussed above, it might have been expected that fenfluramine would reduce photosensitive or induced seizures. Importantly, however, it has surprisingly been found that all types of seizures exhibited by patients with Dravet Syndrome, that is seizures in addition to and other than those that are photosensitive or induced can be suppressed by treatment in accordance with a method of the present invention.

Thus, in context of the present invention, the term "seizure" is used to not only encompass photosensitive or induced seizures, but some or all of the other types of seizures experienced by epileptics, including but not limited to *Status Epilepticus*.

There are a number of genetic mutations that are indicative of Dravet Syndrome. Mutations in the SCN1A (such as partial or total deletion mutations, truncating mutations and/or missense mutations e.g. in the voltage or pore regions S4 to S6), SCN1B (such as the region encoding the sodium channel β1 subunit), SCN2A, SCN3A, SCN9A, GABRG2 (such as the region encoding the γ2 subunit), GABRD (such as the region encoding the δ subunit) and/or PCDH19 genes have been linked to Dravet Syndrome.

Thus, according to a further aspect of the present invention, there is provided a method of treating a patient that exhibits a mutation in one, some or all of the above genes by administering to that patient an effective dose of fenfluramine. In certain embodiments of this aspect of the invention, the patient has been diagnosed with Dravet Syndrome.

Fenfluramine has been known to inhibit serotonin reuptake and to trigger the release of serotonin in the brain due to disruption of its vesicular storage, However, until the present invention was made, it was not known that fenfluramine's mechanism of action made it suitable for the treatment of Dravet Syndrome.

Thus, according to a still further aspect of the present invention, there is provided a method of stimulating one or more 5-HT receptors in the brain of a patient by administering an effective dose of fenfluramine to said patient, said one or more 5-HT receptors being selected from one or more of $5\text{-HT}_1$, $5\text{-HT}_{1A}$, 5 $\text{HT}_{1B}$, $5\text{-HT}_{1C}$, $5\text{-HT}_{1D}$, $5\text{-HT}_{1E}$, $5\text{-HT}_{1F}$, $5\text{-HT}_2$, $5\text{-HT}_{2A}$, $5\text{-HT}_{2B}$, $5\text{-HT}_{2C}$, $5\text{-HT}_3$, $5\text{-HT}_4$, $5\text{-HT}_5$, $5\text{-HT}_{5A}$, $5\text{-HT}_{5B}$, $5\text{-HT}_6$, and $5\text{-HT}_7$ amongst others. In certain embodiments of this aspect of the invention, the patient has been diagnosed with Dravet Syndrome.

In embodiments of the invention, any effective dose of fenfluramine can be employed. However, surprisingly low doses of fenfluramine have been found by the inventors to be efficacious, particularly for inhibiting or eliminating seizures in Dravet Syndrome patients. Thus, in preferred embodiments of the invention, a daily dose of less than about 0.5 mg/kg/day, about 0.45 mg/kg/day, about 0.4 mg/kg/day, about 0.3 mg/kg/day, about 0.25 mg/kg/day or about 0.2 mg/kg/day to about 0.1 mg/kg/day, about 0.05 mg/kg/day, or about 0.01 mg/kg/day is employed. Put differently, a preferred dose is less than about 0.5 to about 0.01 mg/kg/day. Such a dose is less than the daily dose of fenfluramine suggested for administraton to achieve weight loss.

The dose of fenfluramine administered in the methods of the present invention can be formulated in any pharmaceutically acceptable dosage form including, but not limited to oral dosage forms such as tablets including orally disintegrating tablets, capsules, lozenges, oral solutions or syrups, oral emulsions, oral gels, oral films, buccal liquids, powder e.g. for suspension, and the like; injectable dosage forms; transdermal dosage forms such as transdermal patches, ointments, creams; inhaled dosage forms; and/or nasally, rectally, vaginally administered dosage forms. Such dosage forms can be formulated for once a day administration, or for multiple daily administrations (e.g. 2, 3 or 4 times a day administration).

The dosage form of fenfluramine employed in the methods of the present invention can be prepared by combining fenfluramine with one or more pharmaceutically acceptable diluents, carriers, adjuvants, and the like in a manner known to those skilled in the art of pharmaceutical formulation.

In a method of the present invention, fenfluramine can be employed as a monotherapy in the treatment of Dravet Syndrome. Alternatively, fenfluramine can be coadministered simultaneously, sequentially or separately with one or more co-therapeutic agents, such as anticonvulsants. Preferred co-therapeutic agents can be selected from the group consisting of carbamazepine, ethosuximide, fosphenytoin, lamotrigine, levetiracetam, phenobarbitol, progabide, topiramate, stiripentol, valproic acid, vaiproate, verapamil, and benzodiazepines such as clobazam, clonazepam, diazepam, ethyl loflazepate, lorazepam, midazolam. Use of a pharmaceutically acceptable salt of a co-therapeutic agent is also contemplated.

Fenfluramine can be administered in the form of the free base, or in the form of a pharmaceutically acceptable salt, for example selected from the group consisting of hydrochloride, hydrobromide, hydroiodide, maleate, sulphate, tartrate, acetate, citrate, tosylate, succinate, mesylate and besylate. Further illustrative pharmaceutically acceptable salts can be found in Berge et al., *J. Pharm Sci.* (1977) 68(1):1-19.

Fenfluramine for use in the methods of the present invention may be produced according to any pharmaceutically acceptable process known to those skilled in the art. Examples of processes for synthesizing fenfluramine are provided in the following documents: GB1413070, GB1413078 and EP441160.

The dose of fenfluramine to be used in a method of the present invention can be provided in the form of a kit, including instructions for using the dose in one or more of the methods of the present invention. In certain embodiments, the kit can additionally comprise a dosage form comprising one or more co-therapeutic agents.

A method of the present invention can be practiced on any appropriately diagnosed patient. In a typical embodiment of the present invention, the patient is aged about 18 or less, about 16 or less, about 14 or less, about 12 or less, about 10 or less, about 8 or less, about 6 or less or about 4 or less to about 0 months or more, about 1 month or more, about 2 months or more, about 4 months or more, about 6 months or more or about 1 year or more. Thus, the diagnosed patient is typically io about one month old to about 18 years old when treated.

The invention is further illustrated in the following Comparative Example.

COMPARATIVE EXAMPLE 1

The results of two pivotal studies (conducted in France and Italy) that led to approval of stiripentol in the European Union are provided below. In the first table, the number of test subjects who became seizure-free upon co-administration of stiripentol and either valproate or clobazam vs a placebo or two months is provided. In the second table, the number of subjects who exhibited a >50% reduction in the number of seizures following administration of stiripentol and either valproate or clobazam vs a placebo or two months is provided.

TABLE 1

Seizure Free Patients (Treated with Stiripentol and either Valproate or Clobazam vs Placebo)

| | Seizure Free Patients | |
|---|---|---|
| | Stiripentol | Placebo |
| STICLO-France | 9/20 (45%) | 0/16 (0%) |
| STICLO-Italy | 3/11 (27%) | 0/9 (0%) |
| Combined | 12/31 (38.7%) | 0/25 (0%) |

TABLE 2

Responders – >50% Reduction in the Number of Seizures (Treated with Stiripentol and either Valproate or Clobazam vs Placebo)

| | Responders | |
|---|---|---|
| | Stiripentol | Placebo |
| STICLO-France | 15/21 (71.4%) | 1/20 (5%) |
| STICLO-Italy | 8/12 (66.7%) | 1/11 (9.1%) |
| Combined | 23/33 (69.7%) | 2/31 (6.5%) |

The following table provides results based on the data presented in Ceulemans et al., *Epilepsia* (2012) 53(7):1131-1139. Patients were administered an average daily dose of fenfluramine of 0.34 mg/kg/day for between 1 and 22 years.

TABLE 3

Seizure Free Patients and Responders (Treated with Fenfluramine and Valproate)
Fenfluramine

| Seizure-free Patients | >50% Reduction in Seizures |
|---|---|
| 8/12 (66%) | 9/12 (75%) |

As can be seen from the foregoing data, long-term fenfluramine treatment advantageously resulted in a seizure-free condition in 66.6% of test subjects, compared to 38.7% for stiripentol.

Additionally, long-term fenfluramine treatment advantageously resulted in a slightly improved reduction in seizures (75%) as compared to the reduction in seizures in patients treated with stiripentol for two months (69.7%).

These results confirm that fenfluramine provides long term elimination/reduction in seizures to a greater extent than observed with short term administration of the currently approved therapy (in the EU), stiripentol.

These results were achieved, in the vast number of cases, using significantly lower doses of fenfluramine than those proposed previously in the treatment of various conditions typified by seizures. Additionally and surprisingly, fenfluramine effectively reduced the incidence of all types of seizures and not only photosensitive or self-induced seizures.

The subjects treated with fenfluramine were monitored using echocardiography for possible heart valve defects. No clinically relevant defects were identified.

Each of the patents, patent applications and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

The invention claimed is:

1. A method of adjunctive treating, preventing and/or ameliorating seizures in a patient diagnosed with Dravet syndrome, comprising:
    administering to the patient an effective dose of fenfluramine or a pharmaceutically acceptable salt thereof in a dose of 0.2 mg/kg/day to 0.5 mg/kg/day to the patient;
    administering to the patient an effective dose of stiripentol or a pharmaceutically acceptable salt thereof; and
    administering to the patient an effective dose of clobazam or a pharmaceutically acceptable salt thereof; and
    whereby seizures are ameliorated in the patient.

2. A method of adjunctive treating, preventing and/or ameliorating seizures in a patient diagnosed with Dravet syndrome and not responsive to prior treatment, comprising:
    administering to the patient an effective dose of fenfluramine or a pharmaceutically acceptable salt thereof in a dose of 0.5 mg/kg/day to 0.2 mg/kg/day to the patient;
    administering to the patient an effective dose of stiripentol or a pharmaceutically acceptable salt thereof; and
    administering to the patient an effective dose of clobazam or a pharmaceutically acceptable salt thereof; and
    whereby seizures are ameliorated in the patient not responsive to prior treatment.

3. The method of claim 2, wherein the patient is shown to have a genetic mutation selected from the group consisting of SCN1A, SCN1B, SCN2A, SCN3A, SCN9A, GABRG2, GABRD and PCDH19.

4. A method of adjunctive treating, preventing and/or ameliorating seizures, comprising:
    determining a patient has a mutation in a gene which mutation is associated with Dravet syndrome;
    administering to the patient determined to have the mutation:
        (a) 0.2 mg/kg/day of fenfluramine or a pharmaceutically acceptable salt thereof;
        (b) an effective dose of stiripentol or a pharmaceutically acceptable salt thereof; and
        (c) an effective dose of clobazam or a pharmaceutically acceptable salt thereof;
    whereby seizures are ameliorated in the patient exhibiting the mutation.

5. The method as claimed in claim 4, wherein the mutation is selected from the group consisting of SCN1A, SCN1B, SCN2A, SCN3A, SCN9A, GABRG2, GABRD and PCDH19.

* * * * *